United States Patent

Pasczuk et al.

[11] Patent Number: 5,799,657
[45] Date of Patent: Sep. 1, 1998

[54] CONDOM WITH SAFETY RETAINING MEANS

[76] Inventors: Daniel Miguel Pasczuk; Ana Maria Acuna, both of 2063 Juan R. Jimenez St., 1669 Del Viso, Prov. of Bs. As., Argentina

[21] Appl. No.: 888,652

[22] Filed: Jul. 7, 1997

[30] Foreign Application Priority Data

Jul. 12, 1996 [AR] Argentina ............... 337.449

[51] Int. Cl.$^6$ ............................................. A61F 6/04
[52] U.S. Cl. .................................. 128/844; 128/918
[58] Field of Search ............................ 128/842, 844, 128/918; 604/347–353; 600/38–40

[56] References Cited

U.S. PATENT DOCUMENTS 5,111,831  5/1992  Foggia ........................... 128/844
5,158,556  10/1992 Starley ........................... 128/844
5,370,130  12/1994 Hess ............................... 128/844
5,370,131  12/1994 Hess ............................... 128/844

*Primary Examiner*—Michael A. Brown
*Attorney, Agent, or Firm*—Merchant, Gould, Smith, Edell, Welter & Schmidt, P.A.

[57] ABSTRACT

A safety condom of the type including a tubular film wall defining a close distal end and an open proximal end, the open end being defined by a peripheral resilient thick ring, the thin wall being weakened or cut along a circumferential splitting section partially extending around the wall close and adjacent the thick ring, so that this ring defines a safety retaining ring and part of the ring may be stretched away of the open end to be passed around and firmly retained in the wearer's testicles.

17 Claims, 2 Drawing Sheets

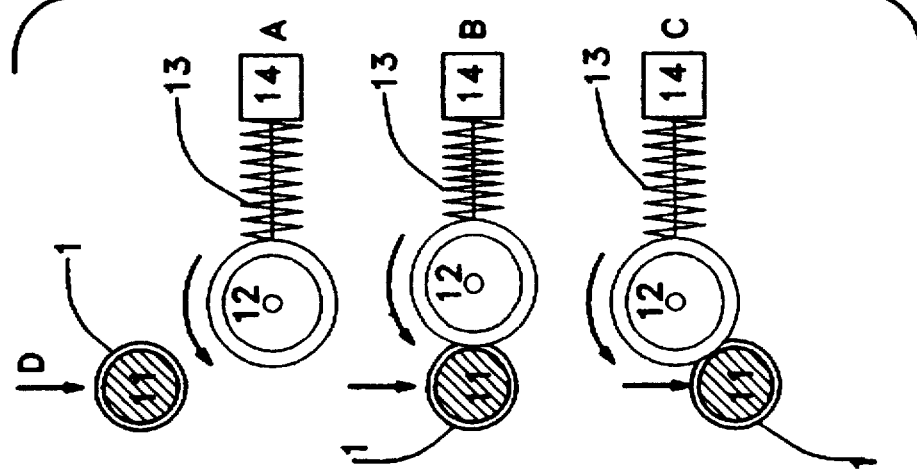
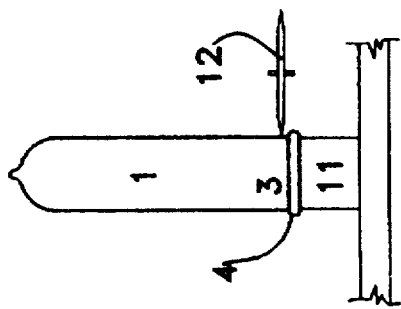
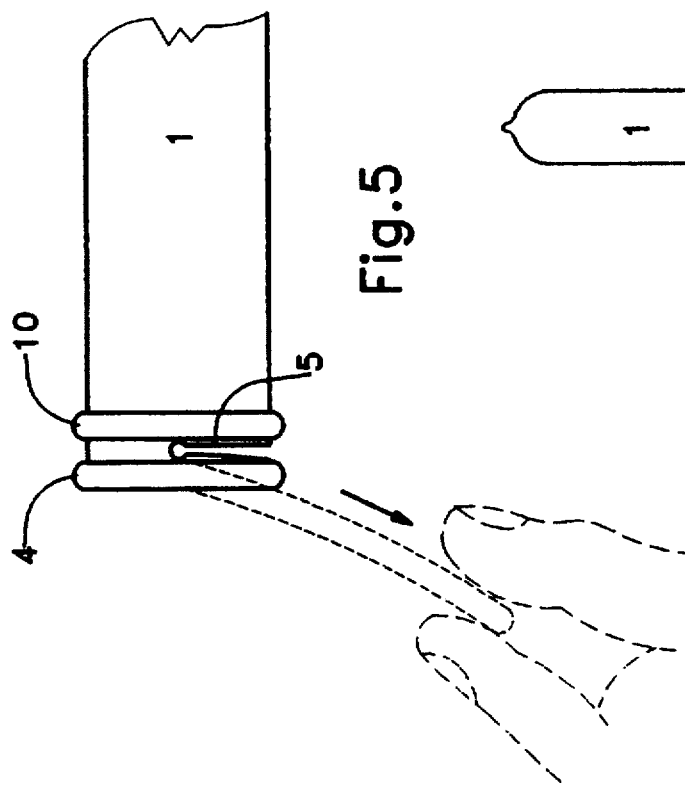

5,799,657

1

CONDOM WITH SAFETY RETAINING MEANS

BACKGROUND OF THE INVENTION

1. Field of the Invention

The present invention relates to a safety condom which condom enables the wearer to use the same without the risk of loosing the condom either during the intensive use thereof or when the masculine member has been decreased in its volume because of the end of the activity for which the condom has been worn.

2. Description of the Prior Art

Many contraceptive are well known in the art, particularly those that must be used by men such as the prophylactics commonly referenced as condoms. These condoms have been used for decades are becoming more and more important due to the transmission of lethal diseases. The condom has been found to be practically the only safe means against these diseases, these condoms, however, have not been improved as to their aspects related to the safety use thereof. Some of them have been improved by the use of new materials which enabled the same to be thinner and thinner. Thus, modern condoms are manufactured with technologies that deliver a thin latex film that provides a natural feeling for the wearer and is resistant and safety. Strict quality controls made these condoms more safe than old ones. These condoms, when properly used, help reduce the risk of catching or spreading many Sexually Transmitted Diseases such as syphilis, gonorrhea, chlamydial infections, genital herpes and HIV (AIDS).

The above aspects related to the transmission of diseases are combined with the use of spermicidal lubricants that reduce the number of active sperm, thereby decreasing the risk of pregnancy. This aspect is particularly important in connection with the present invention because the spermicidal lubricant attempts to kill the sperm in the event the wearer loses his erection before withdrawal and some semen spill outside the condom. Bearing in mind this situation, the wearer must be careful of keeping the condom on when loosing his erection in order to avoid any semen enters into contact with his couple.

The above aspect is so important that the condom's manufacturers recommend that the condom should not be used as a substitute for the combined use of a vaginal spermicide and the condom. Manufacturers also put emphasis in that the condom "may help" reduce the risk of catching and spreading diseases "when properly used", but no precise indications as to the correct use thereof, particularly when erection is loosed, are clearly established. It would be therefore many convenient to have a condom with the necessary safety means to avoid the semen spilling outside the condom upon loosing of erection.

3. Summary of the Invention

It is therefore one object of the present invention to provide a new safety condom which may be used without the need of being alert to the loosing of erection because the risk of spilling semen outside the condom is eliminated or drastically reduced.

It is still another object of the present invention to provide a condom that avoids all the above drawbacks related to conventional condoms and that gives the wearer the guaranty that the condom is correctly positioned and retained during all the time it is being used even when the volume of the penis is dramatically reduced.

It is a further object of the present invention to provide a safety condom of the type comprising a tubular body defining a longitudinal axis and having a thin wall defining a close distal end and an open proximal end, the open end defining a peripheral resilient thick ring, wherein the thin wall includes a circumferential splitting section partially extending around said longitudinal axis and close to said thick resilient ring, whereby a stretching portion of the peripheral ring can be partially stretched away from the condom body to be arranged around the wearer's testicles and retained on the testicles while a stationary portion of the ring being firmly fixed to the condom body.

It is even another object of the present invention to provide a method for manufacturing a condom as defined above, wherein the process comprises the steps of:

providing a thin wall tubular body having a distal closed end and a proximal open end, the open end having a circumferential thick ring;

partially cutting the thin wall tubular body close and adjacent the thick ring, the cut being performed circumferentially around said longitudinal axis of the body.

Briefly, it is another object of the invention to provide a safety condom of the type comprising a tubular film wall defining a close distal end and an open proximal end, the open end being defined by a peripheral resilient thick ring, the thin wall being weakened or cut along a circumferential splitting section partially extending around said wall close and adjacent said thick ring, so that this ring defines a safety retaining ring and part of the ring may be stretched away of the open end to be passed around and firmly retained in the wearer's testicles.

The above and other objects, features and advantages of this invention will be better understood when taken in connection with the accompanying drawings and description.

BRIEF DESCRIPTION OF THE DRAWINGS

The present invention is illustrated by way of example in the following drawings wherein:

FIG. 5 shows a partial sectional side view similar to FIGS. 1, 2, wherein the phantom lines shown how the ring is being stretched away from the condom open end, ready to be passed around the wearer's testicles, to the position shown in FIG. 2;

FIG. 6 schematically shows a condom located onto a support moving along a processing path through a cutting blade, in a method for manufacturing the condom of the invention; and FIG. 7 schematically shows several steps of the method for manufacturing the condom of the invention, with three relative positions between the support/condom and the cutting blade being shown;

DESCRIPTION OF THE PREFERRED EMBODIMENTS

Figure 1:
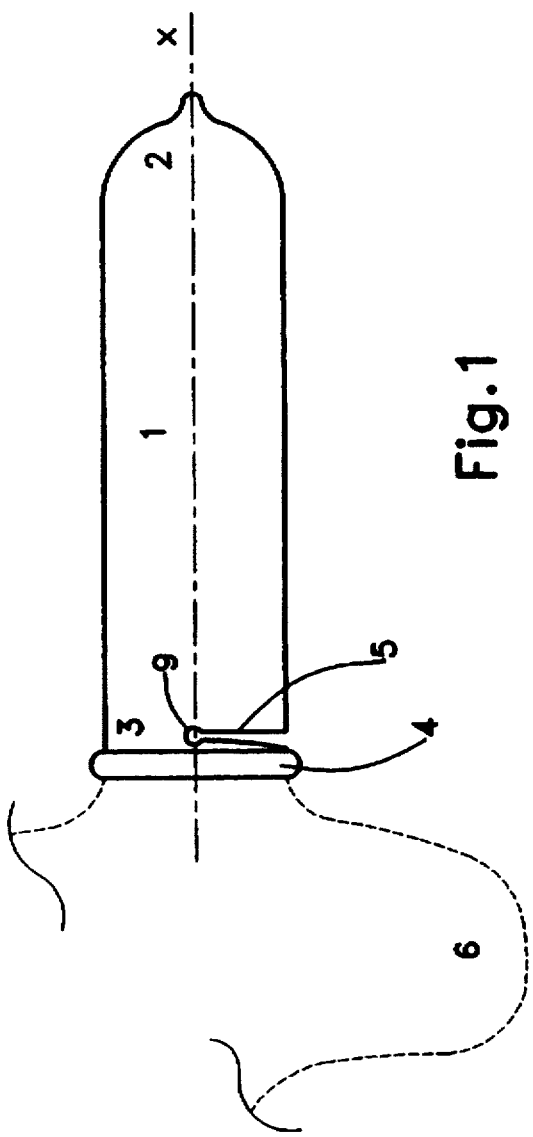
FIG. 1 shows a side view of a preferred embodiment of the condom of the invention worn on a pene's wearer with the safety ring without being stretched, the wearer being shown in phantom lines.

Now referring in detail to the drawings it may be seen from FIG. 1 a condom according to the invention comprising a tubular body 1 having a distal closed end 2 and a proximal open end 3. Like in the conventional condoms, said tubular body 1 is made of a thin wall, from a thin latex film, for example. Open end 3 terminates into a resilient ring 4 and has a splitting section 5 formed in the thin wall of the body and close and adjacent to ring 4. With reference number 6 the testicles of the wearer are shown. With the above described features, ring 4 is a safety retaining ring with the purpose and function as will be described later.

The term "splitting section" means, in accordance within the present description, any section formed in the thin wall of body 1, either by cutting or molding, and defining a weakened or a cut section of the wall with the purpose of being torn off or opened to allow the ring 4 to be partially stretched away from the open end of the condom as will be described later.

In a first preferred embodiment of the invention, as it is shown in FIG. 1, splitting section 5 consists of a cut performed in the wall of the body extending along a circumferential, for example semi-circular, arc around a geometrical longitudinal axis X of the condom. It will be apparent to any person skilled in the art that the extension of the arc of the splitting section will vary according to the size of the condom, material, etc. without departing from the inventive concept of the invention.

Figure 2:
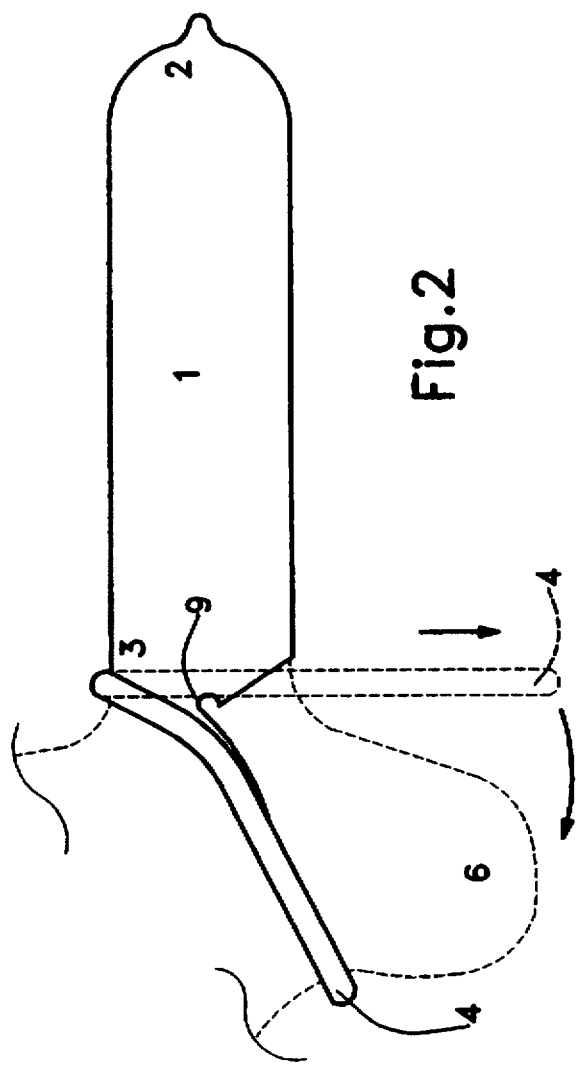
FIG. 2 shows a side view similar to FIG. 2 but with the safety ring stretched and passed around the wearer's testicles for safety retaining purposes.

The purpose of ring 4 is to be taken by the wearer's fingers, as it is shown in FIG. 5, stretched away from the open end of the condom, as depicted by the phantom lines in FIG. 5, and passed around the wearer's testicles, as shown in FIG. 2, to be safely retained onto the pene's wearer without the risk of withdrawal upon loosing erection. FIG. 2. also shows in phantom lines an intermediate position of the ring, stretched in the direction indicated by the arrow, from which intermediate position the ring is then brought around the wearer's testicles and resiliently retained around them.

Figure 3:
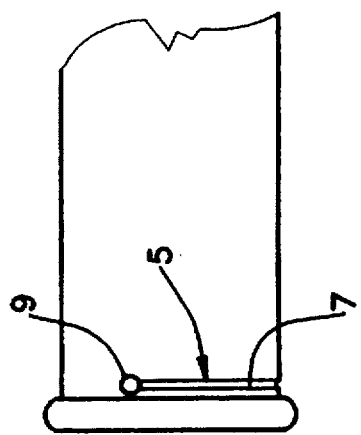
FIG. 3 shows an alternative splitting section consisting of a weakening portion in the condom thin wall and a round cut at the section end.
Figure 4:
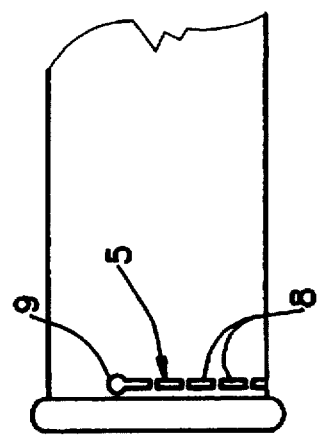
FIG. 4 shows an alternative splitting section consisting of multiple small cuts and a round cut at the section end.

The splitting section may consist also of other forms enabling the wearer to use the condom according the purposes of the invention. Thus, as it is shown in FIG. 3, splitting section 5 may be formed by molding in a weakened section comprising a wall portion 6 of a thickness smaller than the thickness of the remaining entire thin wall of body 1. FIG. 4 shows another alternative wherein splitting section 5 is formed of a plurality of small cuts 8. Both alternatives shown in FIGS. 3, 4 enables the wearer to use the condom either with the retaining ring using the advantages of the invention or like a conventional condom. As far as the weakened wall portion 6 is not torn off or the small cuts 8 are not entirely opened, the condom of the invention behave like a conventional condom.

In all the embodiments shown in FIGS. 1–4 the splitting section has respective opposite ends with a round cut 9 to avoid the thin wall outside the splitting section be torn beyond the ends of the splitting section with the risk of completely tearing the ring off the condom.

FIG. 3 shows another alternative embodiment wherein a second ring 10 is shown to even extremely improve the safety provided by ring 4. Thus, the open end of the condom will be retained against the wearer's penis while the entire condom will be retained against the wearer's penis by the retaining ring 4 around the wearer's testicles. That is, the inventive condom may be used like a conventional condom and with the advantages provided by the invention. Splitting section 5 will be formed between the both rings and may have any of the configurations illustrated in FIGS. 1–4.

Although many processes available for the persons skilled in the art are available for manufacturing the condom of the invention without departing from the inventive concept of the invention, a schematic description will be provided of a preferred method for manufacturing the condom of the invention, particularly the condom shown in FIGS. 1 and 2.

According to the method of the invention a condom, for example a conventional condom, is located, in a tight-fitting manner, onto a vertical cylindrical support 11, as it is shown in FIG. 6. The support with the condom thereon is moved along a processing path passing by a cutting blade 12 which is preferably a rotating cutting disc.

As shown in FIG. 7 blade 12 interferes with the moving path of support 11 with the condom, thus entering into an intimate contact with the condom when the same passing by the location the blade is mounted. Blade 12 is preferably a circular blade with a peripheral cutting edge. The blade is resiliently mounted thank to a compression spring 13 fixed in turn to a mounting means 14 schematically shown. As it is illustrated in three sequences A, B and C, blade 12 is normally in the extended position indicated by sequence A, wherein the contact between the condom and the blade is unavoidable when the support passes through the blade in a cutting station shown by sequence B. When the support enters the cutting station, sequence B, the blade begins to cut the condom in a leading circumferential portion thereof, as seen in the moving direction. The condom is continuously cut during the time passes by the cutting station, through blade 12 and, when leaving the blade position, the condom is finally cut at a rear circumferential portion thereof, as shown by sequence C in FIG. 7.

The cutting action of blade 12 is guaranteed by the pressure exerted by spring 13 which keeps blade 12 always in firm cutting contact against the condom mounted onto support 11. The moving direction of the support is indicated by the straight arrows while the rotation of blade 12 is indicated by the curved arrows.

We claim:

1. A safety condom, comprising:
   a) a tubular body defining a longitudinal axis and having a thin wall defining a closed distal end and an open proximal end;
   b) a peripheral resilient continuous thick ring defined by the open end; and
   (c) wherein the thin wall includes a rectilinear cut partially extending around the longitudinal axis and closely parallel to the peripheral resilient continuous thick ring, whereby a stretching portion of the peripheral resilient continuous thick ring can be partially stretched away from the body to be arranged around testicles of a wearer and retained on the testicles of the wearer while a stationary portion of the peripheral resilient continuous thick ring is firmly fixed to the body.

2. The safety condom of claim 1, wherein the rectilinear cut extends along a semicircular path around the longitudinal axis.

3. The safety condom of claim 1, wherein the rectilinear cut has two opposite ends defining respective perforations to prevent the thin wall from being inadvertently torn along the rectilinear cut and beyond the rectilinear cut ends.

4. The safety condom of claim 1, wherein the open end comprises a pair of peripheral thick adjacent rings and the rectilinear cut is located between both rings.

5. A method for manufacturing a condom, comprising the steps of:
   providing a thin wall tubular body having a distal closed end and a proximal open end, the open end having a peripheral resilient continuous thick ring; and partially rectilinear cutting the thin wall tubular body close and adjacent the peripheral resilient continuous thick ring, the partially rectilinear cutting being performed circumferentially around the longitudinal axis of the body.

6. The method of claim 5, wherein the partial rectilinear cutting step comprises cutting a continuous cut.

7. The method of claim 5, wherein the providing step comprises arranging the condom completely extended over a cylindrical support; and the partial rectilinear cutting step comprises:

moving the cylindrical support with the condom along a processing path passing through a cutting circular blade, partially interfering moving of the cylindrical support with the condom along the processing path, the cutting circular blade being resiliently mounted with a spring effect enough to yield upon the passing of the cylindrical support with the condom but to be in cutting contact with the condom to perform a circumferential cut on the condom.

8. A safety condom, comprising:

a) a tubular body defining a longitudinal axis and having a thin wall defining a closed distal end and an open proximal end;

b) a peripheral resilient thick ring defined by the open end; and c) wherein the thin wall includes a circumferential splitting section partially extending around the longitudinal axis and close to the peripheral resilient thick ring, the circumferential splitting section comprising a weakened section having a thickness smaller than a thickness of the thin wall of the body, whereby a stretching portion of the peripheral resilient thick ring can be partially stretched away from the body to be arranged around testicles of a wearer and retained on the testicles of the wearer while a stationary portion of the peripheral resilient thick ring is firmly fixed to the body.

9. The safety condom of claim 8, wherein the weakened section has two opposite ends defining respective perforations to prevent the thin wall from being inadvertently torn along the weakened section beyond the weakened section ends.

10. The safety condom of claim 8, wherein the circumferential splitting section extends along a semicircular path around the longitudinal axis.

11. The safety condom of claim 8, wherein the open end comprises a pair of peripheral thick adjacent rings and the circumferential splitting section is located between both rings.

12. A safety condom, comprising:

a) a tubular body defining a longitudinal axis and having a thin wall defining a closed distal end and an open proximal end;

b) a peripheral resilient thick ring defined by the open end;

c) wherein the thin wall includes a circumferential splitting section partially extending around the longitudinal axis and close to the peripheral resilient thick ring, the circumferential splitting section comprising a multiple-cut section having a plurality of aligned cuts in the thin wall of the body, whereby a stretching portion of the peripheral resilient thick ring can be partially stretched away from the body to be arranged around testicles of a wearer and retained on the testicles of the wearer while a stationary portion of the peripheral resilient thick ring is firmly fixed to the body.

13. The safety condom of claim 12, wherein the multiple-cut section has two opposite ends defining respective perforations to prevent the thin wall from being inadvertently torn along the multiple-cut section beyond the multiple-cut section ends.

14. The safety condom of claim 12, wherein the circumferential splitting section extends along a semicircular path around the longitudinal axis.

15. The safety condom of claim 12, wherein the open end comprises a pair of peripheral thick adjacent rings and the circumferential splitting section is located between both rings.

16. A method for manufacturing a condom, comprising the steps of:

providing a thin wall tubular body having a closed distal end and an open proximal end, the open end having a circumferential thick ring; and partially cutting the thin wall tubular body close and adjacent the circumferential thick ring, the partially cutting being performed circumferentially around a longitudinal axis of the thin wall tubular body, and wherein the partially cutting comprises performing a plurality of aligned small cuts.

17. The method of claim 16, wherein the providing step comprises arranging the condom completely extended over a cylindrical support; and the cutting step comprises:

moving the cylindrical support with the condom along a processing path passing through a cutting circular blade, partially interfering moving of the cylindrical support with the condom along the processing path, the cutting circular blade being resiliently mounted with a spring effect enough to yield upon the passing of the cylindrical support with the condom but to be in cutting contact with the condom to perform the plurality of aligned small cuts on the thin wall.

* * * * *